May 21, 1957 E. S. BOERNER Plant Pat. 1,603
ROSE PLANT
Filed Sept. 7, 1956
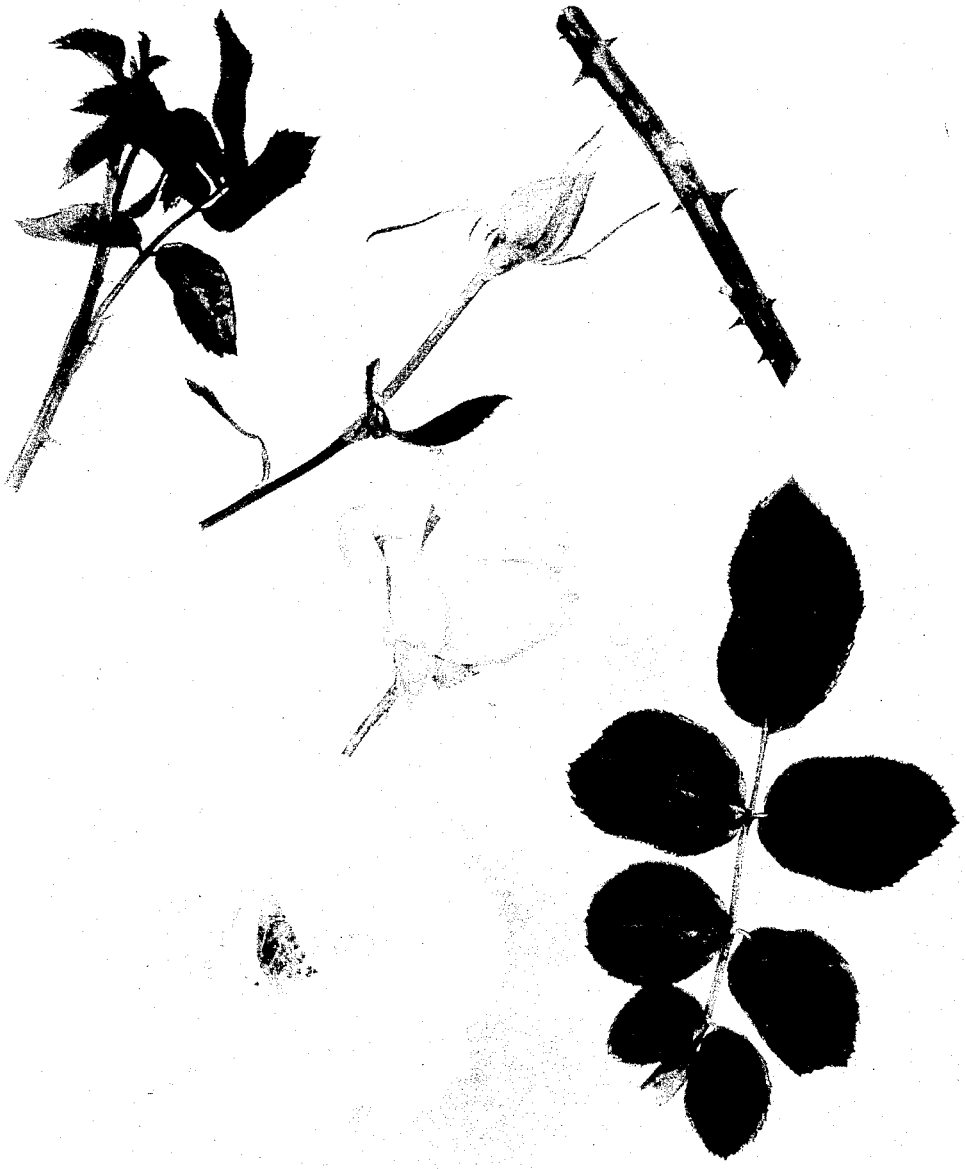
Inventor.
E. S. Boerner
By: Robb & Robb
Attorneys.

United States Patent Office

Plant Pat. 1,603
Patented May 21, 1957

1,603

ROSE PLANT

Eugene S. Boerner, Newark, N. Y., assignor to Jackson & Perkins Company, Newark, N. Y., a corporation of New York Application September 7, 1956, Serial No. 608,642

1 Claim. (Cl. 47—61)

The present invention relates to a new and distinct variety of rose plant of the large-flowered polyantha class, which was originated by me by crossing an unnamed and unpatented floribunda seedling with the well-known variety "Fashion" (Plant Patent No. 789).

The primary objective of this breeeding was to obtain another rose of the "Fashion" family, but having a different shade of flower color, while maintaining the same size of the flower, and which is suitable for both outdoor and greenhouse growing. This objective was fully achieved, along with other improved features, which together represent a new combination in a rose of this class.

The following characteristics, in particular, differentiate the new variety from its parents, as well as from all other varieties of which I am aware:

(1) The habit of producing flowers comparable in size to those of "Fashion," in large clusters and in profuse quantity on each plant;

(2) The good keeping quality of the flowers;

(3) The fruity almond fragrance of the flowers;

(4) The distinctive Shrimp Pink, lightly overcast with Geranium Pink, general color tonality of the flowers; and (5) Its suitability for both outdoor and greenhouse growing.

Asexual reproduction of my new variety of budding, as performed at Newark, N. Y., and also at Pleasanton, California, shows that the aforementioned characteristics and distinctions come true to form and are established and transmitted through succeeding propagations.

The accompanying drawing shows typical specimens of the vegetative growth and the flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed floribunda seedling of 1944.

*Pollen parent.*—"Fashion."

Classification:

*Botanic.*—Large-flowered polyantha.

*Commercial.*—Floribunda.

*Flower*

(Observations made from specimens grown outdoors at Newark, New York, in the early afternoon and in the early part of September.)

Blooming habit: Recurrent—continuous.

Bud:

*Size.*—Medium.

*Form.*—Ovoid; pointed; is not affected by wet or hot weather.

*Color.*—When sepals first divide—Eugenia Red, Plate 13. When petals begin to unfurl—Geranium Pink, Plate 1. When half-blown: inside of petals—Eosine Pink, Plate 1, lightly overcast with Strawberry Pink, Plate 1; reverse of petals—Thulite Pink, Plate 26, lightly overcast with Salmon Buff, Plate 14.

*Sepals.*—Slightly branched; curl back when petals begin to unfurl. Color: inside—Chrysolite Green, Plate 31; outside—Light Cress Green, Plate 31, lightly overcast with Garnet Brown, Plate 1.

*Calyx.*—Color—Absinthe Green, Plate 31. Shape—funnel. Size—small. Aspect—smooth. Odor when rubbed—none.

*Peduncle.* — Length — medium. Aspect — rough. Strength—erect; slender. Color—Garnet Brown, Plate 1.

*Opening.*—Opens up well; is not affected by adverse weather conditions.

Bloom:

*Size.*—Medium. Average size when fully expanded—from 3 to 3½ inches.

*Borne.*—Several together and in columnar clusters.

*Stems.*—Medium length; normal strength.

*Form (when first open).*—Cupped. Permanence—retains its form to the end, but outer petals curl back.

*Petalage.*—Double (full but open center). Number of petals under normal conditions—from 25 to 30.

*Color.*—Center of flower—Eosine Pink, Plate 1, lightly overcast with Shrimp Pink, Plate 1. Outer petals—Pale Salmon, Plate 14, lightly overcast with La France Pink, Plate 1. Base of petals (aiglet)—Citron Yellow, Plate 16. Inside of petals—Shrimp Pink, Plate 1, lightly overcast with Geranium Pink, Plate 1. Reverse of petals—Cameo Pink, Plate 26, lightly overcast with Hermosa Pink, Plate 1. General tonality from a distance—Shrimp Pink, Plate 1, lightly overcast with Eosine Pink, Plate 1.

*Discoloration.*—General tonality at end of first day—Eosine Pink, Plate 1, lightly overcast with Shrimp Pink, Plate 1. Second day—Shrimp Pink, Plate 1, lightly overcast with Eosine Pink, Plate 1. Third day—Pale Salmon, Plate 14, lightly overcast with La France Pink, Plate 1.

Petals:

*Texture.*—Thick; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; small.

*Persistence.*—Drop off cleanly.

*Fragrance.*—Moderate. Nature—fruity almond.

*Lasting quality.*—On the plant—very long. As cut flower—very long.

*Genital organs*

Stamens, anthers: Medium size; many; regularly arranged around styles. Color—Orange-Buff, Plate 3.

Stamens, filaments (threads): Medium length. Color—Picric Yellow, Plate 4.

Pollen: Color—Pale Orange-Buff, Plate 3.

Styles: Columnar; uneven length; medium length; thin.

Stigmas: Color—Capucine Orange, Plate 3.

Ovaries: All enclosed in calyx.

Hips: None.

Seeds: None.

*Plant*

Form: Bush.
Growth: Vigorous; upright, branching; airy growth.
Foliage: Compound of 5 to 7 leaflets.

*Size.*—Medium.

*Quantity.*—Normal.

*Color.*—New foliage: upper side—Forest Green, Plate 17, lightly overcast with Oxblood Red, Plate 1; under side—Oxblood Red, Plate 1. Old foliage: upper side—Dark Cress Green, Plate 31; under side—Light Cress Green, Plate 31.

*Shape.*—Oval pointed.

*Texture.*—Upper side—leathery. Underside—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—smooth.

*Stipules.*—Medium length; slightly bearded.

Wood:

*New wood.*—Color—Garnet Brown, Plate 1. Bark—smooth.

*Old wood.*—Color—Deep Dull Yellow Green, Plate 32. Bark—smooth.

Thorns:

*Thorns.*—Quantity: on mail stalks from base—ordinary; on laterals from stalk—ordinary. Form—narrow base; medium length; straight. Color (when young)—Carmine, Plate 1. Position—irregular.

*Prickles.*—Quantity: on main stalks—none; on laterals—none.

*Short needles.*—Quantity: on main stalks—none; on laterals—none.

I claim:

A new and distinct variety of rose plant of the large-flowered polyantha class, substantially as herein shown and described, characterized particularly as to novelty by the large cluster habit and profusion of its flowers, the good keeping quality of the flowers and their fruity almond fragrance, the distinctive Shrimp Pink, lightly overcast with Geranium Pink, general color tonality of its flowers, and its suitability for both outdoor and greenhouse growing.

No references cited.